United States Patent [19]
Kwok et al.

[11] Patent Number: 6,044,844
[45] Date of Patent: Apr. 4, 2000

[54] MASK AND HARNESS ASSEMBLY

[75] Inventors: Philip Rodney Kwok, West Pymble; Kenneth Frederick Hely, Jannali; Jakob Walter Bruderer, Tuggerah; Colin Edward Sullivan, Birchgrove, all of Australia

[73] Assignee: ResMed Limited, North Ryde, Australia

[21] Appl. No.: 08/982,762

[22] Filed: Dec. 2, 1997

[30] Foreign Application Priority Data

Dec. 2, 1996 [AU] Australia .................................. PO4002

[51] Int. Cl.⁷ .................................................. A62B 18/08
[52] U.S. Cl. ............................... 128/207.11; 128/205.25; 128/206.21; 128/206.27; 128/207.13; 138/117; 138/177
[58] Field of Search ........................ 128/202.27, 205.25, 128/206.21, 206.24, 206.27, 206.28, 207.11, 207.13, 912, DIG. 26; 138/39, 137, 177, 178

[56] References Cited

U.S. PATENT DOCUMENTS

| | | |
|---|---|---|
| Re. 35,339 | 10/1996 | Rapoport . |
| D. 188,084 | 5/1960 | Garelick . |
| D. 231,803 | 6/1974 | Huddy . |
| D. 250,131 | 10/1978 | Lewis et al. . |
| D. 262,322 | 12/1981 | Mizerak . |
| D. 293,613 | 1/1988 | Wingler . |
| D. 310,431 | 9/1990 | Bellm . |
| D. 323,908 | 2/1992 | Hollister et al. . |
| D. 334,633 | 4/1993 | Rudolph . |
| D. 362,061 | 9/1995 | McGinnis et al. . |
| D. 377,089 | 12/1996 | Starr et al. . |
| 781,516 | 1/1905 | Guthrie .............................. 128/206.29 |
| 812,706 | 2/1906 | Warbasse . |
| 1,081,745 | 12/1913 | Johnston et al. .................... 128/207.13 |
| 1,192,186 | 7/1916 | Greene ................................ 128/207.13 |
| 1,653,572 | 12/1927 | Jackson . |
| 1,926,027 | 9/1933 | Biggs . |

(List continued on next page.)

FOREIGN PATENT DOCUMENTS

| | | |
|---|---|---|
| 91/77110 | 11/1991 | Australia . |
| 94/64816 | 12/1994 | Australia . |
| 9516178 | 7/1995 | Australia . |
| 32914/95 | 2/1996 | Australia . |
| 9459430 | 2/1996 | Australia . |

(List continued on next page.)

OTHER PUBLICATIONS

Mask 1 Photographs, Respironics Inc., Reusable Full Mask (small) Part # 452033 Lot #951108.
Mask 2 Photographs, Puritan—Bennett, Adam Curcuit, Shell Part # 231700, Swivel Part # 616329–00, Pillows (medium) Part #616324.

(List continued on next page.)

Primary Examiner—John G. Weiss
Assistant Examiner—Joseph F. Weiss, Jr.
Attorney, Agent, or Firm—Holland & Hart LLP

[57] ABSTRACT

A mask and harness assembly (10). The assembly (10) includes a mask (12) a harness (14) including at least one strap (16) connected to the mask (12) and at least one fluid delivery tube (18) connected to, and in fluid communication with, the mask (12). The strap(s) (16) and the tube(s) (18) being adapted to locate the mask (12) at a predetermined location on the head of the wearer.

14 Claims, 6 Drawing Sheets

U.S. PATENT DOCUMENTS

| | | |
|---|---|---|
| 2,123,353 | 7/1938 | Cat . |
| 2,248,477 | 7/1941 | Lombard . |
| 2,254,854 | 9/1941 | O'Connell . |
| 2,317,608 | 9/1943 | Heidbrink . |
| 2,371,965 | 3/1945 | Lehmberg . |
| 2,376,871 | 5/1945 | Fink . |
| 2,415,846 | 2/1947 | Randall . |
| 2,438,058 | 3/1948 | Kincheloe . |
| 2,578,621 | 12/1951 | Yant . |
| 2,931,356 | 4/1960 | Schwarz . |
| 2,939,458 | 6/1960 | Lundquist . |
| 3,013,556 | 12/1961 | Galleher . |
| 3,182,659 | 5/1965 | Blount et al. . |
| 3,189,027 | 6/1965 | Bartlett . |
| 3,193,624 | 7/1965 | Webb et al. . |
| 3,238,943 | 3/1966 | Holley . |
| 3,315,674 | 4/1967 | Bloom et al. . |
| 3,330,273 | 7/1967 | Bennett . |
| 3,362,420 | 1/1968 | Blackburn et al. . |
| 3,363,833 | 1/1968 | Laerdal . |
| 3,556,122 | 1/1971 | Laerdal . |
| 3,580,051 | 5/1971 | Blevins . |
| 3,700,000 | 10/1972 | Hesse et al. . |
| 3,720,235 | 3/1973 | Schrock ................................. 138/137 |
| 3,796,216 | 3/1974 | Schwarz . |
| 3,799,164 | 3/1974 | Rollins ............................... 128/205.25 |
| 4,077,404 | 3/1978 | Elam . |
| 4,167,185 | 9/1979 | Lewis . |
| 4,226,234 | 10/1980 | Gunderson . |
| 4,245,632 | 1/1981 | Houston . |
| 4,304,229 | 12/1981 | Curtin . |
| 4,328,797 | 5/1982 | Rollins, III et al. . |
| 4,347,205 | 8/1982 | Stewart . |
| 4,354,488 | 10/1982 | Bartos . |
| 4,402,316 | 9/1983 | Gadberry . |
| 4,412,537 | 11/1983 | Tiger ................................. 128/204.17 |
| 4,467,799 | 8/1984 | Steinberg . |
| 4,522,639 | 6/1985 | Ansite et al. . |
| 4,558,710 | 12/1985 | Eichler . |
| 4,616,647 | 10/1986 | McCreadie . |
| 4,622,964 | 11/1986 | Flynn . |
| 4,655,213 | 4/1987 | Rapoport et al. . |
| 4,665,570 | 5/1987 | Davis . |
| 4,671,271 | 6/1987 | Bishop et al. . |
| 4,677,975 | 7/1987 | Edgar et al. . |
| 4,677,977 | 7/1987 | Wilcox . |
| 4,739,755 | 4/1988 | White et al. . |
| 4,770,169 | 9/1988 | Schmoegner et al. . |
| 4,774,941 | 10/1988 | Cook . |
| 4,782,832 | 11/1988 | Trimble et al. . |
| 4,799,477 | 1/1989 | Lewis . |
| 4,809,692 | 3/1989 | Nowacki et al. . |
| 4,819,629 | 4/1989 | Jonson . |
| 4,821,713 | 4/1989 | Bauman . |
| 4,841,953 | 6/1989 | Dodrill . |
| 4,848,334 | 7/1989 | Bellm . |
| 4,848,366 | 7/1989 | Aita et al. . |
| 4,907,584 | 3/1990 | McGinnis . |
| 4,910,806 | 3/1990 | Baker et al. . |
| 4,919,128 | 4/1990 | Kopala et al. . |
| 4,938,210 | 7/1990 | Shene . |
| 4,938,212 | 7/1990 | Gnook et al. . |
| 4,944,310 | 7/1990 | Sullivan ............................... 128/205.25 |
| 4,971,051 | 11/1990 | Toffolon . |
| 4,986,269 | 1/1991 | Hakkinen . |
| 4,989,596 | 2/1991 | Macris et al. . |
| 4,989,599 | 2/1991 | Carter . |
| 5,005,568 | 4/1991 | Loescher et al. . |
| 5,005,571 | 4/1991 | Dietz . |
| 5,038,776 | 8/1991 | Harrison et al. . |
| 5,042,473 | 8/1991 | Lewis . |
| 5,042,478 | 8/1991 | Kopala et al. . |
| 5,046,200 | 9/1991 | Feder . |
| 5,063,922 | 11/1991 | Hakkinen . |
| 5,069,205 | 12/1991 | Urso . |
| 5,109,839 | 5/1992 | Blaselell et al. .................... 128/203.12 |
| 5,109,840 | 5/1992 | Daleiden . |
| 5,121,745 | 6/1992 | Israel . |
| 5,133,347 | 7/1992 | Huennebeck . |
| 5,140,980 | 8/1992 | Haughey et al. . |
| 5,140,982 | 8/1992 | Bauman . |
| 5,159,938 | 11/1992 | Laughlin ................................ 128/858 |
| 5,178,138 | 1/1993 | Walstrom et al. . |
| 5,231,983 | 8/1993 | Matson et al. . |
| 5,233,978 | 8/1993 | Callaway ........................... 128/205.25 |
| 5,243,971 | 9/1993 | Sullivan et al. . |
| 5,265,595 | 11/1993 | Rudolph . |
| 5,279,289 | 1/1994 | Kirk . |
| 5,280,784 | 1/1994 | Kohler . |
| 5,311,862 | 5/1994 | Blasdell et al. .................... 128/205.25 |
| 5,322,057 | 6/1994 | Raabe et al. . |
| 5,343,878 | 9/1994 | Scarberry et al. . |
| 5,357,951 | 10/1994 | Ratner . |
| 5,372,130 | 12/1994 | Stern et al. . |
| 5,388,571 | 2/1995 | Roberts et al. . |
| 5,404,871 | 4/1995 | Goodman et al. . |
| 5,419,318 | 5/1995 | Tayebi . |
| 5,429,126 | 7/1995 | Bracken . |
| 5,429,683 | 7/1995 | Le Mitouard . |
| 5,431,158 | 7/1995 | Tirotta . |
| 5,438,981 | 8/1995 | Starr et al. . |
| 5,441,046 | 8/1995 | Starr et al. . |
| 5,477,852 | 12/1995 | Landis et al. . |
| 5,479,920 | 1/1996 | Piper et al. . |
| 5,488,948 | 2/1996 | Dubruille et al. . |
| 5,492,116 | 2/1996 | Scarberry et al. . |
| 5,501,214 | 3/1996 | Sabo . |
| 5,509,404 | 4/1996 | Lloyd et al. . |
| 5,517,986 | 5/1996 | Starr et al. . |
| 5,538,000 | 7/1996 | Rudolph ............................ 128/205.25 |
| 5,540,223 | 7/1996 | Starr et al. . |
| 5,542,128 | 8/1996 | Lomas . |
| 5,546,936 | 8/1996 | Virag et al. . |
| 5,560,354 | 10/1996 | Berthon-Jones et al. . |
| 5,570,682 | 11/1996 | Johnson . |
| 5,570,689 | 11/1996 | Starr et al. . |
| 5,592,938 | 1/1997 | Scarberry et al. . |
| 5,608,647 | 3/1997 | Rubsamen et al. . |
| 5,642,730 | 7/1997 | Baran . |
| 5,647,355 | 7/1997 | Starr et al. . |
| 5,647,357 | 7/1997 | Barnett et al. . |
| 5,649,532 | 7/1997 | Oren . |
| 5,649,533 | 7/1997 | Griffiths . |
| 5,655,520 | 8/1997 | Howe et al. . |
| 5,655,527 | 8/1997 | Scarberry et al. . |
| 5,657,493 | 8/1997 | Ferrero et al. . |
| 5,657,752 | 8/1997 | Landis et al. . |
| 5,662,101 | 9/1997 | Ogden et al. ....................... 128/205.25 |
| 5,666,946 | 9/1997 | Langenback . |
| 5,685,296 | 11/1997 | Zdrojkowski et al. . |
| 5,687,715 | 11/1997 | Landis et al. . |
| 5,715,814 | 2/1998 | Ebers . |
| 5,746,201 | 5/1998 | Kidd . |
| 5,813,423 | 9/1998 | Kirchgeorg . |
| 5,832,918 | 11/1998 | Pantino . |

FOREIGN PATENT DOCUMENTS

| | | |
|---|---|---|
| 41018/97 | 4/1998 | Australia . |
| 89312/98 | 1/1999 | Australia . |
| 1039144 | 9/1978 | Canada . |
| 0 054 154 | 10/1981 | European Pat. Off. . |
| 0 252 052 A1 | 1/1988 | European Pat. Off. . |

| | | |
|---|---|---|
| 0 264 772 A1 | 4/1988 | European Pat. Off. . |
| 0 386 605 A1 | 2/1990 | European Pat. Off. . |
| 0427474 A2 | 5/1991 | European Pat. Off. . |
| 0 462 701 A1 | 12/1991 | European Pat. Off. . |
| 0 608 684 A1 | 8/1994 | European Pat. Off. . |
| 0 697 225 | 7/1995 | European Pat. Off. . |
| 178 925 A2 | 4/1996 | European Pat. Off. . |
| 0 747 078 A2 | 12/1996 | European Pat. Off. . |
| 0 821 978 | 2/1998 | European Pat. Off. . |
| 2 574 657 A1 | 6/1986 | France . |
| 2 658 725 A1 | 8/1991 | France . |
| 2 749 176 | 12/1997 | France . |
| 459104 | 4/1928 | Germany . |
| 701 690 | 1/1941 | Germany . |
| 71690 | 1/1941 | Germany ................. 128/207.13 |
| 159396 | 6/1981 | Germany . |
| 3015279 A1 | 10/1981 | Germany . |
| 3345067 A1 | 6/1984 | Germany . |
| 3537507 A1 | 4/1987 | Germany . |
| 3539073 A1 | 5/1987 | Germany . |
| 4004157 C1 | 4/1991 | Germany . |
| 4343205 A1 | 6/1995 | Germany . |
| 197 35 359 | 1/1998 | Germany . |
| 297 23 101 | 7/1998 | Germany . |
| 298 10 846 U1 | 8/1998 | Germany . |
| 9/216240 | 8/1997 | Japan . |
| 1395391 | 5/1975 | United Kingdom . |
| 1 467 828 | 3/1977 | United Kingdom . |
| 2145335 | 3/1985 | United Kingdom . |
| 2147506 | 5/1985 | United Kingdom . |
| 2 164 569 | 3/1986 | United Kingdom . |
| 2 267 648 | 12/1993 | United Kingdom . |
| WO 80/01044 | 5/1980 | WIPO . |
| WO 82/03548 | 10/1982 | WIPO ................. 128/207.13 |
| WO 86/06969 | 12/1986 | WIPO . |
| WO 87/01950 | 4/1987 | WIPO . |
| WO 91/03277 | 3/1991 | WIPO . |
| WO 92/15353 | 9/1992 | WIPO . |
| WO 92/20395 | 11/1992 | WIPO . |
| WO 93/01854 | 2/1993 | WIPO . |
| WO 94/02190 | 2/1994 | WIPO ................. 128/207.13 |
| WO 94/16759 | 8/1994 | WIPO . |
| WO 94/20051 | 9/1994 | WIPO . |
| WO 95/02428 | 1/1995 | WIPO . |
| WO 96/17643 | 6/1996 | WIPO . |
| WO 96/25983 | 8/1996 | WIPO . |
| WO 96/39206 | 12/1996 | WIPO . |
| WO 97/07847 | 3/1997 | WIPO . |
| WO 97/41911 | 11/1997 | WIPO . |
| WO 98/04310 | 2/1998 | WIPO . |
| WO 98/11930 | 3/1998 | WIPO . |
| WO 98/18514 | 5/1998 | WIPO . |
| WO 98/24499 | 6/1998 | WIPO . |
| WO 98/26829 | 6/1998 | WIPO . |
| WO 98/26830 | 6/1998 | WIPO . |
| WO 98/48878 | 11/1998 | WIPO . |

OTHER PUBLICATIONS

Mask 3, Photographs, DeVilbiss Healthcare Inc., DeVilbiss Seal–Ring and CPAP Mask Kit (medium), Part 73510–669.

Mask 4 Photographs, Respironics Inc., Monarch Mini Mask with Pressure Port. Part # 572004, Monarch Headgear, Part # 572011.

Mask 5 Photographs, Healthdyne Technologies, Nasal CPAP Mask (medium narrow), Part # 702510.

Mask 6 Photographs, Healthdyne Technologies, Soft Series Nasal CPAP Mask, Part # 702020.

Mask 7 Photographs, DeVilbiss Healthcare Inc., Small Mask and Seal Rings, Part # 73510–668.

Mask 8 Photographs, Respironics Inc., Reusable Contour Mask (medium), Part # 302180.

Mask 9 Photographs, Healthdyne Technologies, Healthdyne Large Headgear.

Mask 10 Photographs, Respironics Inc., Soft Cap (medium), Part # 302142.

Mask 11 Photographs, Weinmann: Hamburg, Nasalmaskensystem mit Schalldämpfer (medium), Part # WN 23105.

Mask 12 Photographs, Life Care.

Mask 13 Photographs, Healthdyne Technologies.

Mask 14 Photograph, King System.

Mask 15 Photographs, Respironics Inc., Paediatric Mask.

Mask 16 Photographs, Hans Rudolph Inc., Hans Rudolph Silicone Rubber Face Mask/8900.

Fig. 8 ns of the present invention will now be
MASK AND HARNESS ASSEMBLY

FIELD OF THE INVENTION

The present invention relates to a mask and harness assembly.

The invention will be described with reference to a nasal mask located on the head of the wearer by a harness for the administration of continuous positive airway pressure (CPAP) treatment. However, it will be appreciated that the invention is not limited to this particular use and is equally suited for use with, for example, facemasks, nasal prongs or mouthmasks, and for treatments including assisted respiration or mechanical ventilation.

BACKGROUND OF THE INVENTION

Hitherto, masks have been located on a wearer's face by a harness formed from straps extending from the mask around the wearer's head and/or neck. A hollow tube is generally attached to the mask, independent of the harness, to supply a breathable gas such as air to the wearer.

This arrangement has several disadvantages. Firstly, the tube is often inadvertently pulled by movement of the wearer, particularly during sleep, which can dislodge the mask and adversely affect gas delivery to the patient's airways, thereby reducing treatment effectiveness.

Another disadvantage is that the mask, straps and tube are prone to entanglement which increases the difficulty of correctly installing the mask and harness.

The present invention seeks to overcome or at least ameliorate these problems with the prior art.

SUMMARY OF THE INVENTION

The present invention provides a mask and harness assembly, the assembly includes a mask, a harness including at least one strap connected to the mask and at least one fluid delivery tube connected to, and in fluid communication with, the mask, wherein the strap(s) and the tube(s) are adapted to locate the mask at a predetermined location on the head of the wearer.

Preferably, the harness includes three straps and one tube. In other configurations, the harness can include two straps and two tubes or one strap and three tubes.

In an embodiment, a first end of two of the straps are connected to a lower portion of the mask and one of the straps and a fist end of one fluid delivery tube are connected to an upper portion of the mask. In another embodiment, a first end of two of the straps are connected to an upper portion of the mask and a first end of one of the straps and one fluid delivery tube are connected to a lower portion of the mask. In both these embodiments the harness includes a cap portion positioned, in use, on the rear of the wearer's skull to which a second end of the three straps and tube are connected.

In a further embodiment, the harness assembly includes one strap connected at each end to the mask and extending around the wearer's head and one tube connected to the mask and the strap.

The tube is preferably crush resistant. Desirably, the tube is also flexible.

In another form, the tube is relatively rigid and is shaped to conform to the wearer's face over which it lies. The tube can also include an outer sheath to improve comfort.

In a preferred form, the tube includes an inner wall defining a passageway through which fluid can pass, and one or more inwardly directed ribs depending from the inner wall, and wherein, on inwardly-directed compression of the tube, the distal edge portion of one or more of said ribs engages an opposed portion of the tube inner wall to maintain said passageway at least partially open.

In a particularly preferred form, the one or more ribs are arranged to run along the longitudinal axis of the tube. The tube can have many cross-sectional shapes, and, in one advantageous form, is substantially retangular having planar top and bottom portions and curved side portions. In such an arrangement, the ribs depend from the top and/or bottom portions to, on upwardly or bottomwardly directed compression, engage the respective opposed top and/or bottom portion inner wall.

The tube is preferably coupled by a connector having a hollow male plug of complementary shape to said tube inner wall and adapted to be received therein. The plug terminates in a plenum chamber internal of the connector, the plenum chamber being in communication with a socket that can be received into said mask or a port coupling of said mask.

BRIEF DESCRIPTION OF THE DRAWINGS

Embodiments of the present invention will now be described with reference to the drawings in which.

DETAILED DESCRIPTION OF PREFERRED EMBODIMENTS

Figure 1:
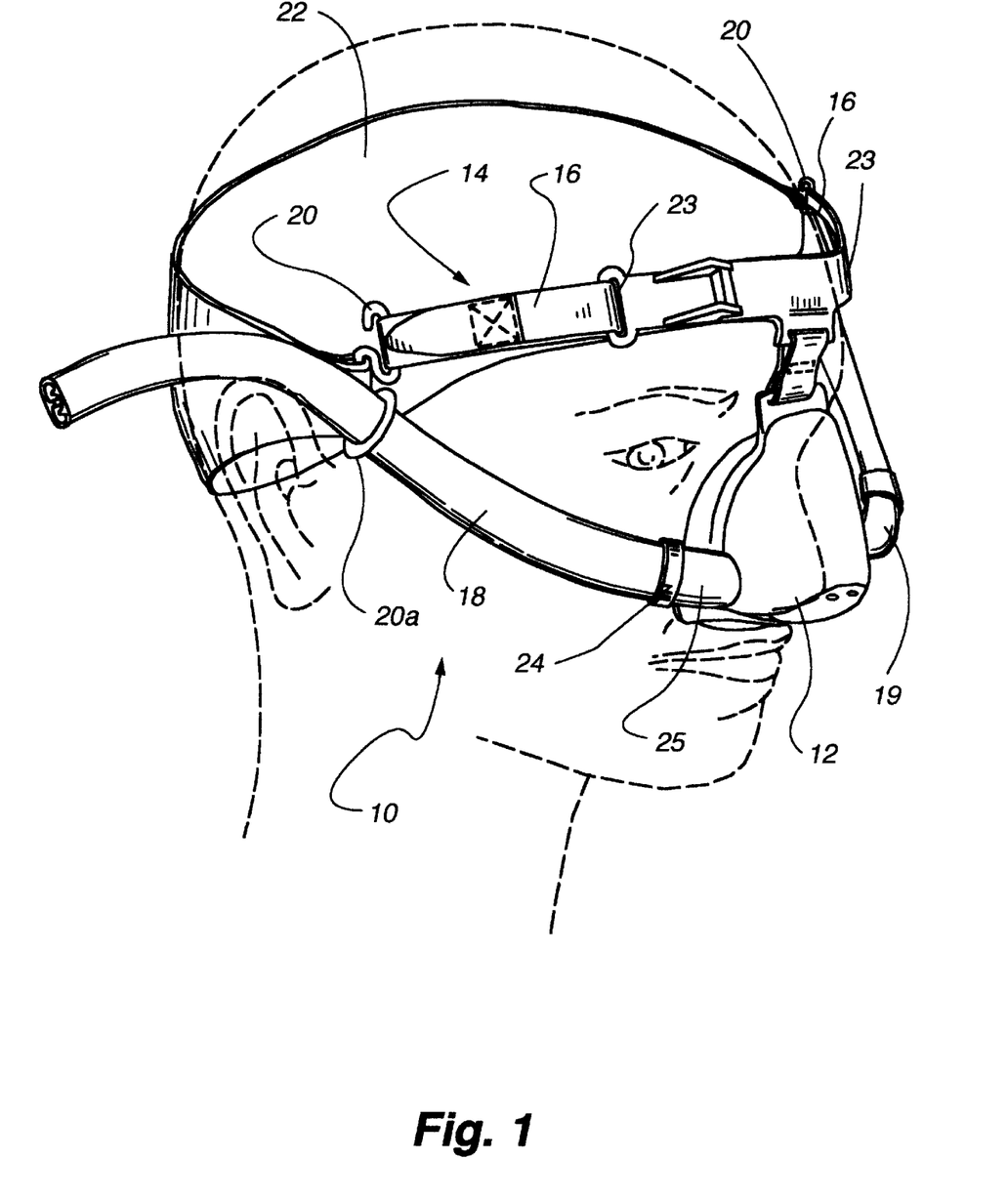
FIG. 1 shows a perspective view of a mask and harness assembly in accordance with a first embodiment of the invention.

Referring to FIG. 1, there is shown a first embodiment of a mask and harness assembly 10 according to the present invention. The assembly 10 includes a nosemask 12 and a harness, indicated generally at 14. The harness 14 includes left and right-hand upper length adjustable straps 16, a right-hand lower length adjustable strap 19 and a left-hand fluid delivery tube 18. The straps and the tube extend from the mask to a yoke 20 attached to a semi-circular cap portion 22. The straps are connected to the mask 12 through apertures 23. The fluid delivery tube 18 is connected to, and in fluid communication with, the mask 12 by virtue of coupling 24 which engages a coupling port 25 extending from the mask.

The fluid delivery tube 18 acts min the manner of a strap and is length adjustable by virtue of its frictional engagement with a lower portion 20a of the yoke 20.

Figure 2:
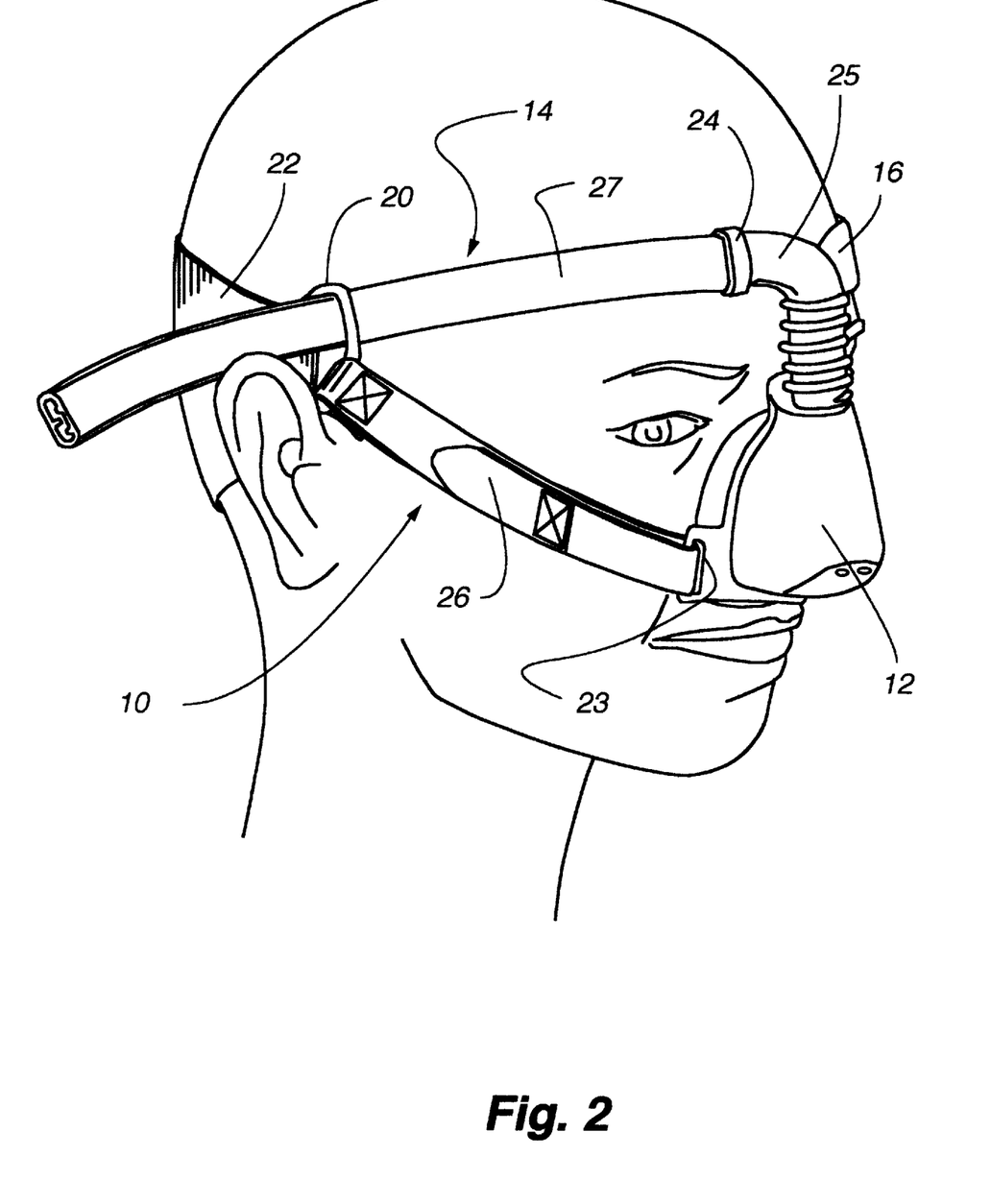
FIG. 2 shows a perspective view of a mask and harness assembly in accordance with a second embodiment of the invention.

FIG. 2 shows a second embodiment of a mask and harness assembly according to the invention in which like reference numerals are used to indicate like features. In this second embodiment, the harness includes left and right lower length adjustable straps 26 (right hand not shown), an upper fluid delivery tube 27 and upper right-hand length adjustable strap 16.

Figure 3:
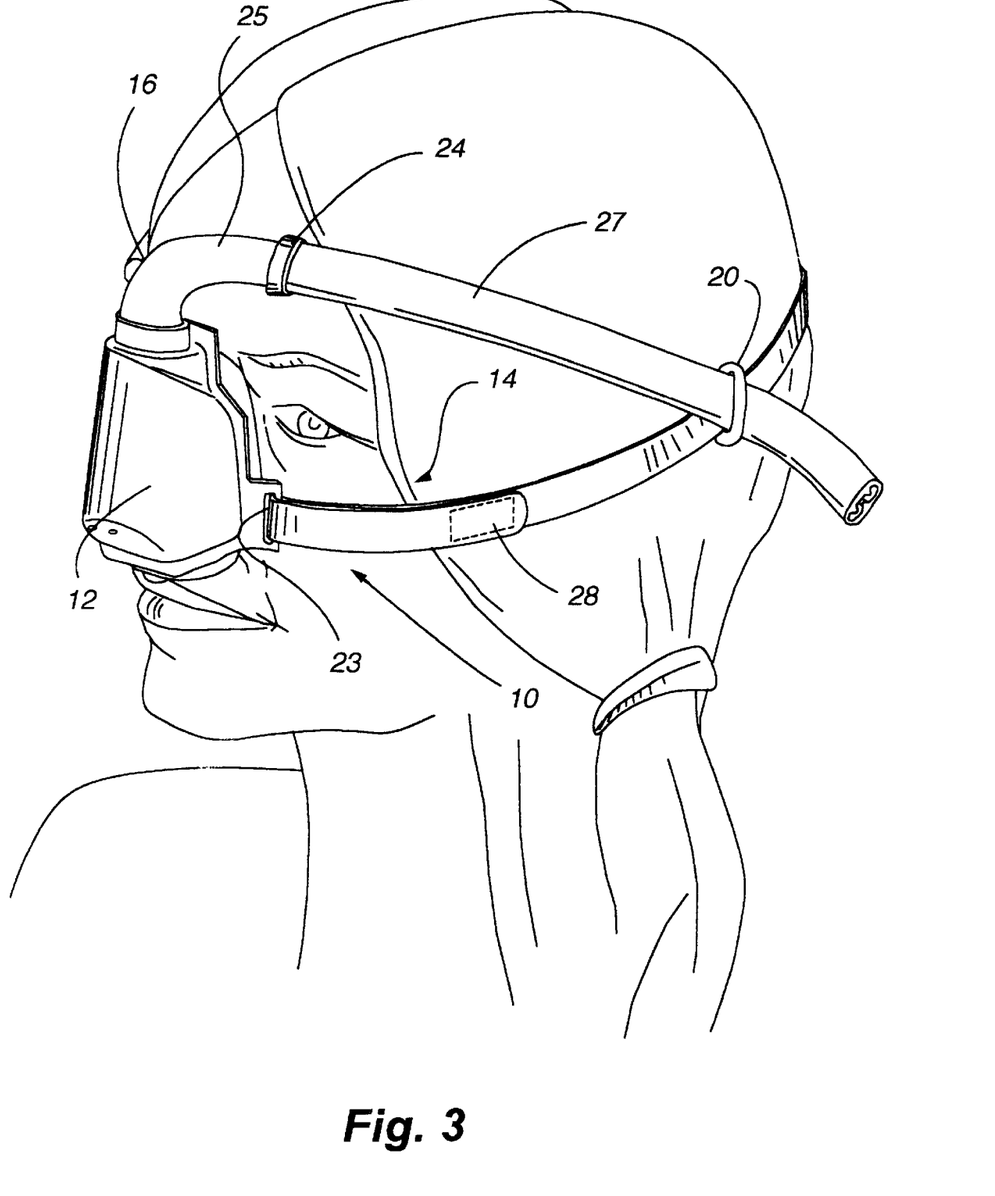
FIG. 3 shows a perspective view of a mask and harness assembly in accordance with a third embodiment of the invention.

FIG. 3 shows a third embodiment of a mask and harness assembly according to this invention in which a single length adjustable lower strap 28 extending from the mask and encircling the head is used in place of the dual lower straps and cap portion shown previously.

Figure 4:
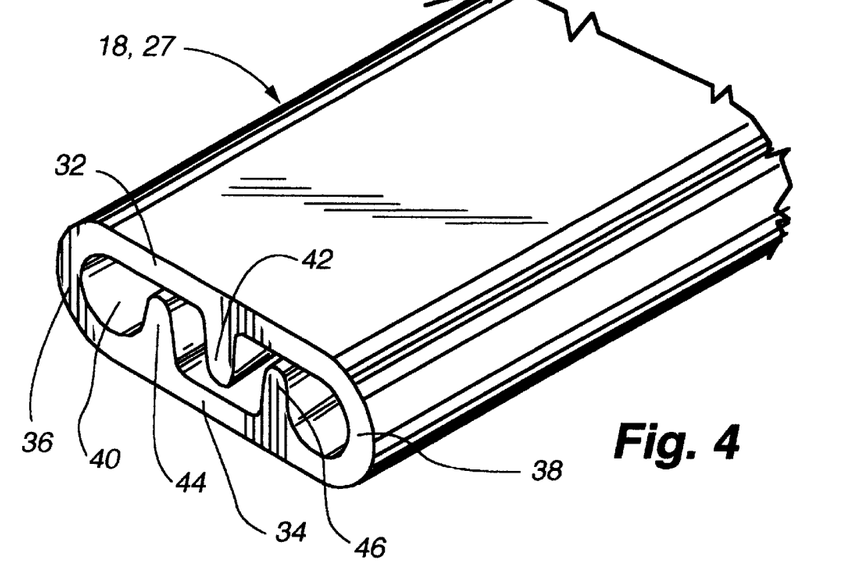
FIG. 4 shows a crush resistant delivery tube used in the mask and harness assembly according to the invention.

FIG. 4 shows a preferred form of fluid delivery tubing 18, 27. The tubing 18 is of substantially rectangular cross-section having flat top and bottom walls 32,34 and curved or rounded side walls 36,38. A passageway 40 through which gas to be delivered can pass is defined within the boundaries of the top, bottom and side walls 32–38.

Figure 5:
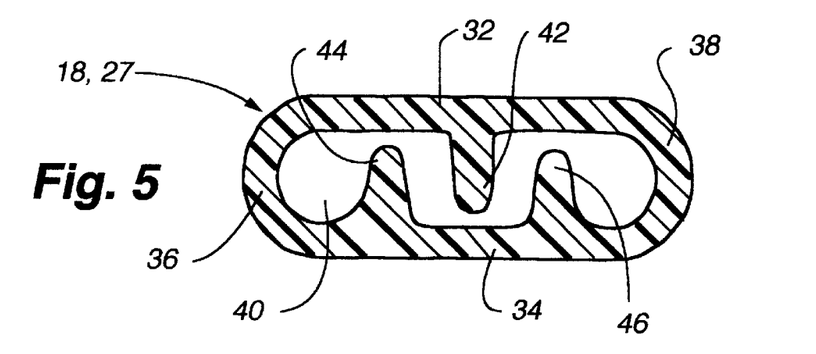
FIG. 5 shows the tube of FIG. 4 in vertical cross-section.
Figure 6:
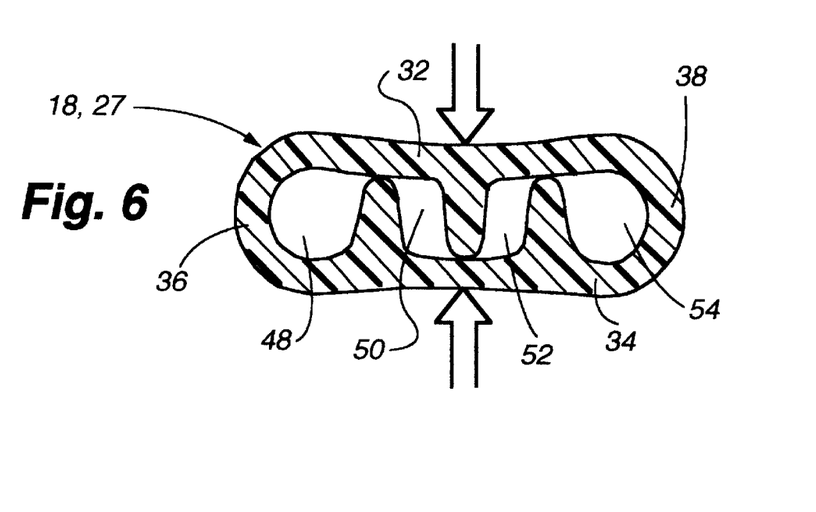
FIG. 6 shows the tube of FIG. 5 when crushed.

As best can be seen from FIGS. 5 and 6, depending downwardly from the top wall 32 is a longitudinally extending rib 42, and in a similar manner, upwardly directed ribs 44,46 depend from the bottom wall 34. Each rib is formed generally by a base and a distal edge portion. FIG. 5 shows a situation where the tubing 18 is in its normal state whereby the single passageway 40 is open to the flow of gas. As shown in FIG. 6, on a vertically directed compressional force, such as would occur on crushing or kinking, the top and bottom walls 32,34 deflect in the direction shown, resulting in the distal edge portions ribs 42–46 respectively engaging an opposed portion of either the top or bottom walls respectively. The result is four separate passageways 48, 50, 52 and 54 in the vicinity of the region of crushing rather than the single passageway 40 in the nucrushed state. The reduction in cross-sectional area is represented by the area between the distal edge portion of each of the ribs and the opposed respective top or bottom wall.

The substantially rectangular cross-sectional shape tends to avoid occlusion of the passageway 40 on the occurrence of laterally directed crushing, in that the passageway 40 would tend to become generally more circular in cross-sectional shape.

The embodiment shown has three depending ribs, however it is equally the case that any convenient number of ribs can be utilised, including a single rib.

The tube 18, 27, in the preferred form shown, is extruded from an elastomeric material of hardness nominally between 35 and 55 Shore A. In the use of the crush resistant fluid delivery tubing 18 for the purposes of CPAP treatment, it is preferable that the reduction in internal cross-sectional area due to crushing be less than 40%, which allows for minimal disruption of flow rates and back pressure, thus maintaining therapeutic treatment pressures.

One particular preferred embodiment suitable for delivering air or breathable gas continuously at a pressure elevated above atmospheric pressure (viz., CPAP treatment) has three internal ribs as shown in FIGS. 4–6, the nominal dimensions are as follows: outside transverse peripheral "circumference" 22 mm, height 8.5 mm and a nominal wall thickness 1.75 mm. The internal cross-sectional area therefore is approximately 52 mm$^2$. This configuration is equivalent to a circular tube of internal diameter 8.0 mm. On compression, as shown in FIG. 6, the total internal cross-sectional area becomes approximately 34 mm$^2$. This is equivalent to a circular tube having an internal diameter of 6.6 mm.

Figure 7:
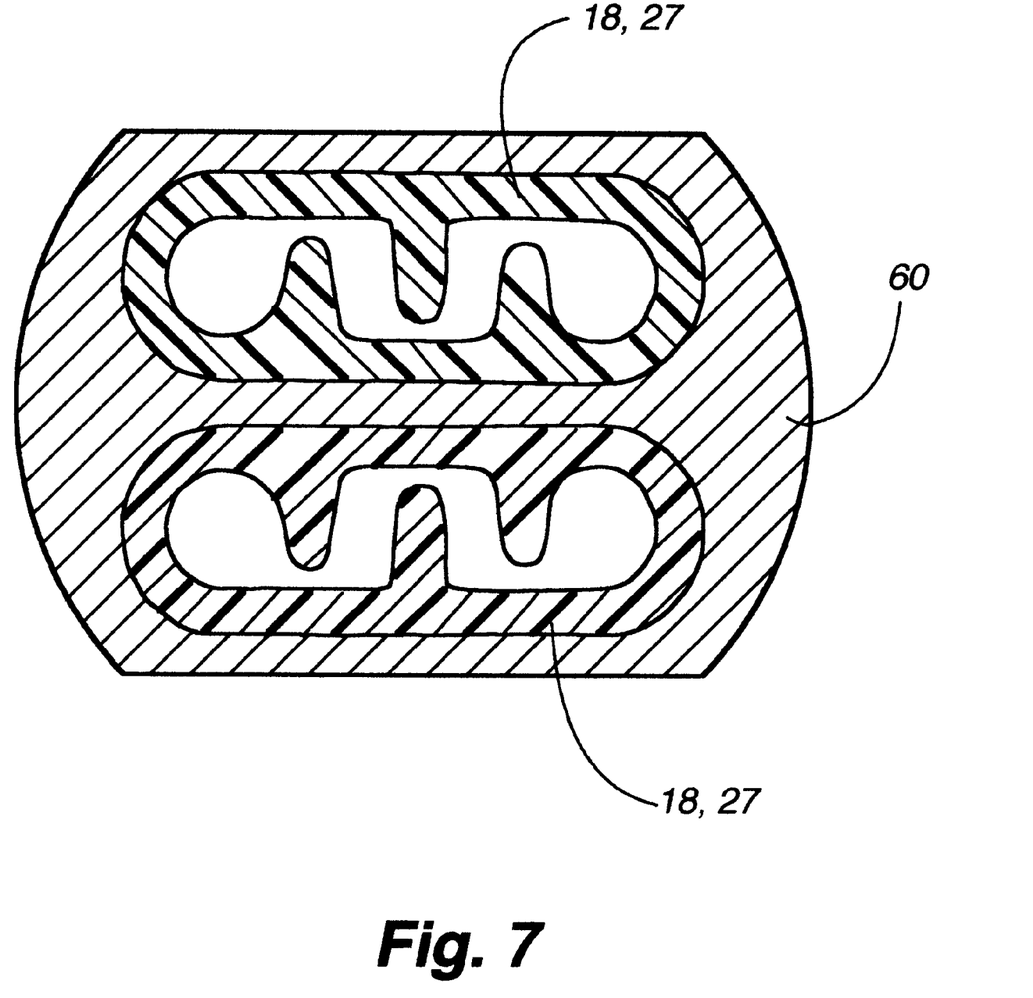
FIG. 7 shows a double passage crush resistant delivery tube.

FIG. 7 shows another embodiment where there are two of the tubes 18, 27, in a vertical stacked arrangement lying within a unifying elastomeric sheath 60. Many other arrangements whereby a multiple number of tubes 18 can be arranged within a single sheath can be provided. Advantages of such independent multiple lubes 18 are that a number of gases or liquids can be delivered without mixing, gases at different pressures can be delivered and/or one of the tubes can be used to provide a feedback signal of mask pressure to a control system.

Figure 8:
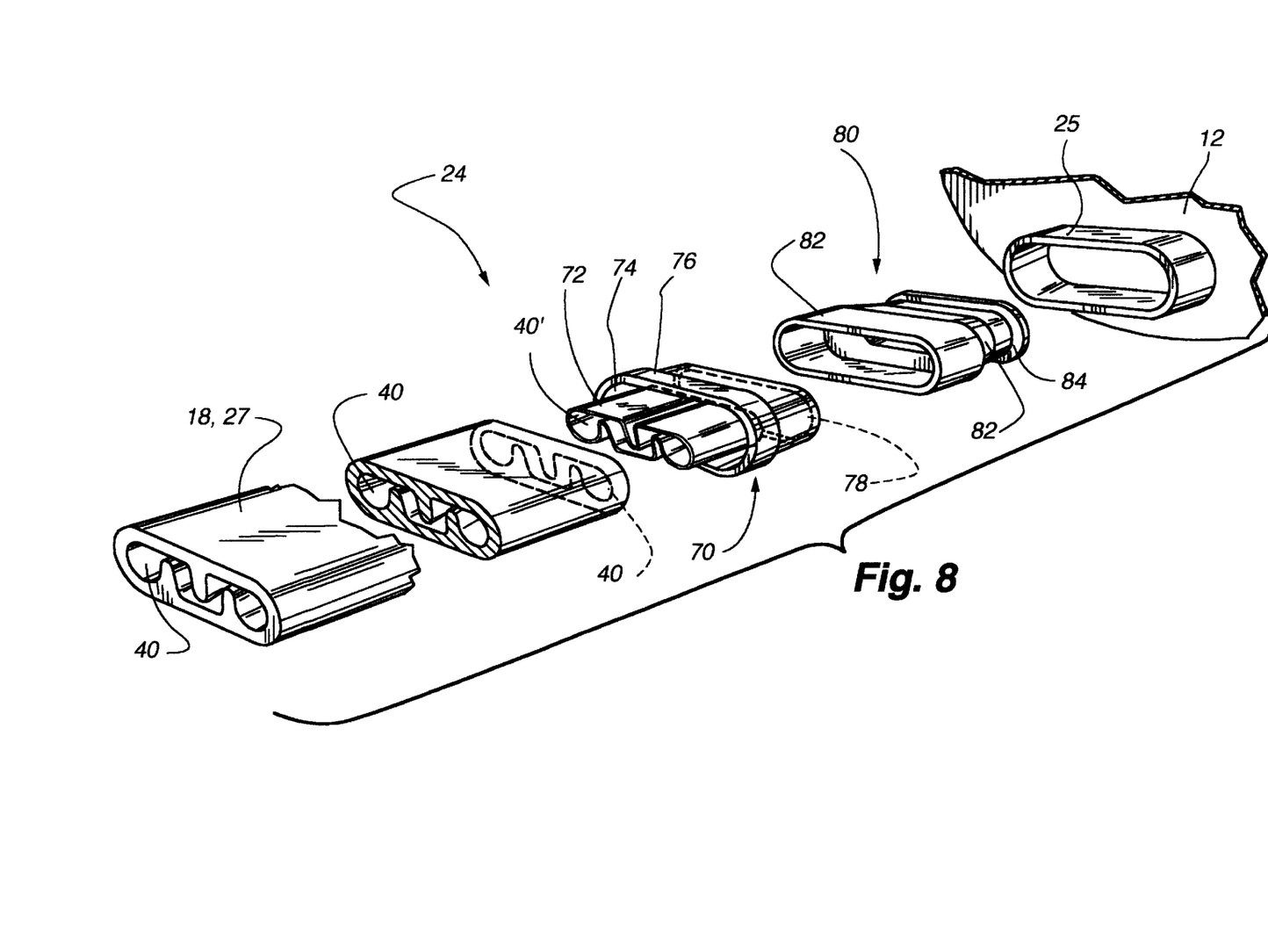
FIG. 8 shows a coupling assembly for use of the delivery tube of FIG. 4 to a single bore tube or mask.

FIG. 8 shows a coupling arrangement 24 between an end of the gas delivery tube 18, 27, previously described and a coupling port 25 of the mask 12. An intermediate connector 70 has an extending hollow male plug 72 of complementary shape to the inner walls defining the passageway 40 of the tube 18,27 to be received therein. The end portion of the tube 18,27 is received within a recess 74 formed by a collar 76 of the connector 70. The plug 72 terminates into a chamber 78 that is received within the port 25. In another embodiment, an air vent insert 80 also is provided that has a socket 82 within which to receive the end of the connector 70 defining the chamber 78, and intermediate air venting region 82 and a flange 84 to be received within the mask port 25 at the other end. All couplings shown and described are preferably achieved by means of a frictional fit, although non-toxic adhesives or mechanical fastenings such as clamps can be used if desired.

Further, if desired, die connector 70 and insert 80 can be omitted and the tube 18, 27 can be directly attached to the port 25.

Industrial Applicability

The invention simplifies mask and harness assembly construction by combining one of the straps and the fluid delivery tube into a single component.

In a preferred form, the tubing has a large frictional contact area with the head and thereby is more resistant to pulling, resulting in more secure mask placement in comparison to the independent tube configurations. The large contact area also reduces the pressure of the tube on the wearer's face, thereby increasing wearer comfort.

Further, the substantially rectangular cross section of the preferred tubing is also comfortable and familiar to the wearer as it lays flat against the head in a similar manner to existing straps. Also, the low profile of the preferred tubing reduces the likelihood of the tube being inadvertently knocked or moved by the wearer.

Numerous alterations and modifications, as would be apparent to one skilled in the art, are to be considered as falling within the ambit of the present invention, embodiments of which have been hereinbefore described.

We claim:

1. A mask and harness assembly, comprising:
    a mask; and
    a harness having at least one strap connected to the mask and at least one crush resistant fluid delivery tube connected to and in fluid communication with the mask, the at least one crush resistant fluid delivery tube having a substantially rectangular cross-sectional profile when in an uncompressed position defined by at least two opposed longer sides and two opposed shorter sides,
    wherein the at least one strap and the at least one crush resistant fluid delivery tube are adapted to locate the mask at a predetermined location on the head of a wearer and the at least one crush resistant fluid delivery tube is adapted to be positioned with one of its longer sides adjacent the skin of the wearer.

2. The assembly as claimed in claim 1, further comprising:
    a cap portion extending about and adapted to be positioned on the rear of the wearer's skull, said cap portion having a first and second end;

a second strap having a first end coupled to a top portion of the mask, and a second end coupled to said first end of said cap portion;

a third strap having a first end coupled to a top portion of the mask, and a second end coupled to said second end of said cap portion;

wherein said at least one strap has a first end coupled to a bottom portion of the mask, and a second end coupled to said second end of said cap portion; and wherein said at least one crush resistant fluid delivery tube has a first end coupled to the bottom portion of the mask, and a body portion coupled to said first end of the cap portion.

3. The assembly as claimed in claim 1, wherein the two opposed longer sides of the fluid delivery tube are each substantially flat.

4. The assembly as claimed in claim 3, wherein the tube has curved side portions.

5. The assembly as claimed in claim 2, further comprising:

a yoke connecting said first end of said cap to said second end of said second strap and to said body portion of said at least one crush resistant fluid delivery tube.

6. The assembly as claimed in claim 2, wherein said body portion of said at least one crush resistant fluid delivery tube is coupled to said cap portion so that said tube is positioned substantially adjacent an upper portion of an ear of the wearer.

7. The assembly as claimed in claim 1, wherein said at least one crush resistant fluid delivery tube further comprises:

a first crush resistant tube portion including an inner wall defining a passageway through which fluid can pass, and one or more inwardly directed ribs depending from the inner wall, wherein upon compression of the first crush resistant tube portion, the distal edge portion of one or more of said ribs engages an opposing portion of the inner wall to maintain said passageway at least partially open during compression;

a second crush resistant tube portion including an inner wall defining a passageway through which fluid can pass, and one or more inwardly directed ribs depending from the inner wall, wherein upon compression of the second crush resistant tube portion, the distal edge portion of one or more of said ribs engages an opposing portion of the inner wall to maintain said passageway at least partially open during compression, and a sheath encasing said first and second crush resistant tube portions.

8. The assembly as claimed in claim 1, wherein the tube has a low cross-sectional profile.

9. The assembly as claimed in claim 1, wherein the tube is flexible.

10. The assembly as claimed in claim 1, wherein tube is covered by an outer sheath.

11. The assembly as claimed in claim 1, wherein the tube is coupled by a connector having a hollow male plug of complementary shape to said tube inner wall and adapted to be received therein, the plug terminating in a plenum chamber internal of the connector, the plenum chamber being in communication with a socket that can be received into said mask.

12. The assembly as claimed in claim 1, wherein the tube includes an inner wall defining a passageway through which fluid can pass, and one or more inwardly directed ribs depending from the inner wall, and wherein on compression of the tube, a distal edge portion of one or more of said ribs engages an opposed portion of the inner wall to maintain said passageway at least partially open.

13. The assembly as claimed in claim 12, wherein the one or more ribs are arranged to run along the longitudinal axis of the tube.

14. The assembly as claimed in claim 12, wherein the ribs on compression, engage the respective opposed portion of the inner wall.

* * * * *